United States Patent

Hsu et al.

[11] Patent Number: 5,840,336
[45] Date of Patent: Nov. 24, 1998

[54] TWO-PHASE MATRIX FOR SUSTAINED RELEASE DRUG DELIVERY DEVICE

[75] Inventors: Tsung-Min Hsu, Union City; Tung Fen Chen, Sunnyvale, both of Calif.

[73] Assignee: Cygnus, Inc., Redwood City, Calif.

[21] Appl. No.: 474,693

[22] Filed: Jun. 7, 1995

Related U.S. Application Data

[60] Division of Ser. No. 56,076, Apr. 30, 1993, which is a continuation-in-part of Ser. No. 956,635, Oct. 5, 1992, abandoned.

[51] Int. Cl.⁶ .......................... A61K 9/14; A61K 31/38; A61K 47/02; A61M 37/00
[52] U.S. Cl. .......................... 424/484; 424/448; 424/449; 424/469; 514/965
[58] Field of Search ........................... 424/484, 485, 424/486, 487, 488, 448, 449, 469, 682; 514/965; 540/575

[56] References Cited

U.S. PATENT DOCUMENTS

| | | |
|---|---|---|
| 4,559,222 | 12/1985 | Enscore et al. |
| 4,668,232 | 5/1987 | Cordes et al. |
| 4,668,506 | 5/1987 | Bawa |
| 4,713,244 | 12/1987 | Bawa et al. |
| 4,737,410 | 4/1988 | Kantner |
| 4,814,173 | 3/1988 | Song et al. |
| 4,826,686 | 5/1989 | Brantl et al. |
| 4,857,313 | 8/1989 | Song et al. |
| 4,880,633 | 11/1989 | Loper et al. |
| 4,882,352 | 11/1989 | Horn |
| 4,885,308 | 12/1989 | Horn ........................ 514/438 |
| 4,898,920 | 2/1990 | Lee et al. |
| 4,904,247 | 2/1990 | Therriault et al. |
| 4,906,463 | 3/1990 | Cleary et al. |
| 4,959,208 | 9/1990 | Chakrabarti et al. ........ 424/486 |
| 4,996,199 | 2/1991 | Minaskanian et al. |
| 4,996,226 | 2/1991 | Horn |

(List continued on next page.)

FOREIGN PATENT DOCUMENTS

| | | |
|---|---|---|
| 0068777 | 1/1983 | European Pat. Off. |
| 0249475 | 12/1987 | European Pat. Off. |
| 0273700 | 7/1988 | European Pat. Off. |
| 0274431 | 7/1988 | European Pat. Off. |
| 0326278 | 8/1989 | European Pat. Off. |
| 0358903 | 3/1990 | European Pat. Off. |
| 0391172 | 10/1990 | European Pat. Off. |
| 0452837 | 10/1991 | European Pat. Off. |
| 0 760 238 A1 | 5/1995 | European Pat. Off. |
| DD 294867 | 10/1991 | Germany |
| WO 89/07935 | 9/1989 | WIPO |

OTHER PUBLICATIONS

Complete English translation of German Patent Publication No. DD 294867 (Oct. 17, 1991) for Polyglot International. (5 pages total).

Berthod et al., "Dry adsorbed emulsions: An oral sustained drug delivery system" *Journal of Pharmaceutical Sciences* (1988) 77(3):216–221.

Naoyuki et al., "DAT–582, a novel serotonin$_3$ receptor antagonist, is a protent and long–lasting antiemetic agent in the ferret and dog" *Journal of Pharmacology and Experimental Therapeutics* (1992) 260(3):1159–1165.

Ulman et al., "Drug permeability of modified silicone polymers" Part I, *Journal of Controlled Release* (1989) 10:251–260.

Ulman et al., "Drug permeability of modified silicone polymers" Part III, *Journal of Controlled Release* (1989) 10:273–281.

*Primary Examiner*—Robert H. Harrison
*Attorney, Agent, or Firm*—Morrison & Foerster LLP

[57] ABSTRACT

A two-phase hydrophilic drug-containing matrix for use in transdermal drug delivery patches in which one phase is a continuous hydrophobic polymer phase which optionally includes a hydrophobic solvent that acts as a skin permeation enhancer and the other phase is a dispersed particulate hydrated inorganic silicate in whose absorbed aqueous phase the drug is dissolved.

12 Claims, 1 Drawing Sheet

U.S. PATENT DOCUMENTS

| | | |
|---|---|---|
| 5,019,378 | 5/1991 | Allen . |
| 5,028,435 | 7/1991 | Katz et al. . |
| 5,035,894 | 7/1991 | Lee et al. . |
| 5,071,645 | 12/1991 | Johnson et al. . |
| 5,071,657 | 12/1991 | Oloff et al. . |
| 5,118,676 | 6/1992 | Minaskanian et al. . |
| 5,118,692 | 6/1992 | Peck . |
| 5,166,341 | 11/1992 | Kon et al. . |
| 5,204,119 | 4/1993 | Shiobara et al. ............. 424/489 |
| 5,225,407 | 7/1993 | Oakley et al. ............. 514/215 |
| 5,232,702 | 8/1993 | Pfister et al. ............. 424/448 |
| 5,300,291 | 4/1994 | Sablotsky et al. ............. 424/78.18 |
| 5,300,299 | 4/1994 | Sweet et al. ............. 424/448 |

TWO-PHASE MATRIX FOR SUSTAINED RELEASE DRUG DELIVERY DEVICE

CROSS-REFERENCE TO RELATED APPLICATION

This application is a division of application Ser. No. 08/056,076 filed Apr. 30, 1993, which is a continuation-in-part of application Ser. No. 07/956,635 filed Oct. 5, 1992, now abandoned.

DESCRIPTION

TECHNICAL FIELD

The present invention is in the field of controlled or sustained release drug formulations and relates specifically to a two-phase drug-containing matrix that may be used as a component in a transdermal patch.

BACKGROUND

In general there are two types of transdermal patch designs: a "reservoir" type and a "matrix" type. In the reservoir type the drug, typically in fluid form, is contained within a walled reservoir whose basal surface is permeable to the drug. In the matrix type the drug is dispersed in a polymer layer, typically an adhesive, and the matrix directly contacts the skin. Both types of device also typically include a backing layer and an inner release liner layer that is removed prior to use.

The present invention concerns a matrix-type device in which the matrix includes a particulate hydrated hydrophilic material that contains the drug and defines at least a portion of the basal surface area of the matrix.

Several prior patents describe two-phase matrixes used in transdermal drug devices, but all are distinct from the matrixes of the present invention.

U.S. Pat. No. 4,668,232 describes a matrix for a transdermal patch which comprises a water-insoluble adhesive, drug that is soluble in the adhesive, and a water-swellable polymer. The inclusion of the water-swellable polymer is alleged to increase the release rate of drug from the matrix.

EPA 0391172 describes a transdermal patch having a matrix composed of a water-insoluble material that contains islands of a solid solution of drug in a water-soluble/swellable polymer and an underlayer that controls the amount of water vapor passing from the skin to the matrix. The matrix is said to be activated by water vapor from the skin.

U.S. Pat. No. 4,559,222 describes a transdermal matrix-type patch in which the matrix is composed of a mixture of mineral oil, polyisobutylene (an adhesive), and colloidal silicon dioxide. The addition of the silicon dioxide allegedly affects the flow characteristics of the mineral oil-polyisobutylene mix.

U.S. Pat No. 5,071,657 describes a transdermal patch matrix of a drug-containing gel that is dispersed in a cross-linked silicone polymer. This matrix is apparently not adhesive as the patent teaches the use of a separate peripheral adhesive layer to affix the patch to the skin.

EPA 0452837A2 describes an adhesive matrix composed of a hydrophobic polymer, a hydrophilic drug, a hydrophilic swellable polymer, water, and a permeation enhancer. The water is said to act as a solubilizer for the drug and the hydrophilic swellable polymer acts to facilitate the mixing of the ingredients and improve the stability of the matrix.

The invention provides a novel matrix composed of a continuous hydrophobic domain and a dispersed particulate hydrated silicate domain which may be used to administer hydrophilic drugs in a sustained manner. The invention permits hydrophilic drugs to be effectively dispersed in a hydrophobic phase, maintains separation of the drug from the hydrophobic phase so that potential interaction between the two is reduced, and provides enhanced release of hydrophilic drugs from matrixes composed of a continuous hydrophobic domain.

DISCLOSURE OF THE INVENTION

One aspect of the invention is a sustainedrelease drug formulation comprising a matrix of:
 (a) a continuous hydrophobic polymer phase;
 (b) a particulate phase dispersed in the continuous polymer phase comprised of:
  (i) a hydrated inorganic silicate;
  (ii) a water-soluble drug at least partly dissolved in the aqueous phase of (i); and
 (c) a dispersing agent for dispersing (b) in (a)
wherein the particulate phase defines at least a portion of the surface area of the matrix and provides a diffusion pathway for the drug in the matrix.

Another aspect of the invention is a transdermal patch comprising a laminated composite of:
 (a) a backing layer; and
 (b) a layer of the above-described matrix
wherein the continuous hydrophobic polymer phase is a pressure sensitive adhesive.

BRIEF DESCRIPTION OF THE DRAWINGS

The drawing is a cross-sectional view (not to scale) of a transdermal patch that includes the matrix formulation of the invention.

Modes for Carrying Out the Invention

Figure 1:
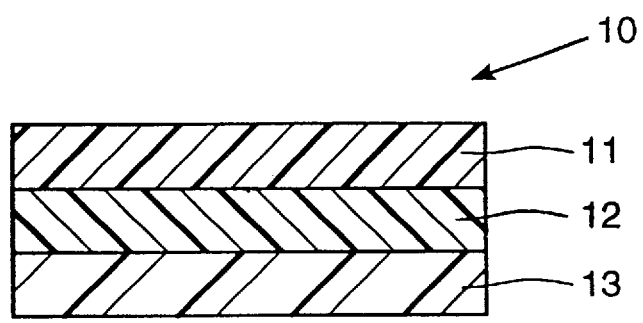

As used herein with respect to the continuous phase, the term "hydrophobic" intends that the material is less than 20% by weight soluble in water at 32° C., over 24 hr.

As used herein, the term "substantially insoluble" intends a solubility of less than about 1% by weight, more usually less than about 0.5% by weight.

As used herein the term "continuous" intends a phase that is interconnected and not separated into distinct domains, segments, or particles.

As used herein with respect to the drug, the terms "hydrophilic" and "water soluble" are intended to be synonymous and to denote that the drug has a water solubility of at least about 0.1 mg/L, preferably at least about 1 mg/L at 32° C.

The term "hydrated" intends that the dispersed particulate material comprises all or a portion of its total absorptive capacity of absorbed aqueous phase (i.e. water and/or other polar solvent).

The term "sustained release" intends a formulation that is capable of releasing a therapeutically effective amount of drug over a time period of one to seven days.

The material that constitutes the continuous phase or hydrophobic domain of the matrix is a hydrophobic polymer that is capable of being mixed with the other components of the matrix and formed into a layer or film. When the matrix is used as the drugcontaining matrix of a transdermal patch, the hydrophobic polymer preferably has pressure-sensitive adhesive properties that permit the matrix to adhere to living human skin for a sustained period of time, i.e., usually at least about one to seven days. Because the polymer is hydrophobic, the drug is substantially insoluble and immiscible in the polymer. Specific examples of polymers that may be used as the continuous hydrophobic phase of the matrix are polysiloxanes, polyisobutylene, solvent-based hydrophobic polyacrylates, polyurethanes, plasticized ethylene-vinyl acetate copolymers, low molecular weight polyether block amide copolymers, styrene-butadiene polymers, and vinyl acetate-based adhesives. The hydrophobic polymer will normally constitute about 30% to 95% by weight of the matrix, more usually 40% to 60% by weight. Other hydrophobic materials such as solvents or permeation enhancers may be included in the hydrophobic domain of the matrix. Examples of such materials are fatty acids (oleic and stearic acid), isopropyl myristate (IPM), fatty acid esters (e.g., propylene glycol monolaurate, polyethylene glycol monolaurate (PEGML), methyl oleate, oleyl oleate), fatty alcohols (e.g., oleyl alcohol), and terpenoids (limonene, menthol, β-pinene, and geraniol).

The dispersed inorganic silicate is in the form of particles that are typically in the non-colloidal size range of 0.001 to 0.1 mm (largest dimension), more usually 0.01 to 0.05 mm. In its hydrated form the material will normally contain about 15% to 600% of its own weight in absorbed water, more usually 100% to 500% of its own weight in water (measured at 25° C.). Other hydrophilic polar solvents such as ethanol, propylene glycol, low molecular weight (200 to 400 mw) polyethylene glycol, isopropyl alcohol, butanediol, m-pyrol and benzyl alcohol may be substituted for water or included in the hydrophilic domain of the matrix. These solvents may be used to increase the solubility of the drug in the absorbed aqueous phase. The hydrated silicate should be stable in the presence of the other components of the matrix and not adversely interact therewith. The loading and particle size of the silicate phase should be such that diffusion pathways defined by the aqueous component of the phase be available for the drug to diffuse from within the matrix to the surface of the matrix. In other words, there is substantial particle-to-particle contact in the dispersed phase. The unhydrated silicate will normally constitute about 2% to 20% by weight of the matrix, more usually 4% to 10% by weight. The silicate may be synthetic, purified, or in a natural form (e.g., clay or talcum). Calcium, magnesium and aluminum silicates and mixtures thereof are preferred. Calcium silicates which have high water and oil absorptions (i.e., >400% by weight) are particularly preferred.

The particulate hydrated silicate is dispersed uniformly throughout the matrix and will define a portion of the surface area of the matrix. That portion should be sufficiently great to provide the desired flux of drug from the matrix. When the matrix is adhesive and is intended to adhere to skin, the portion should not be so great as to cause the matrix to lack sufficient adhesiveness to the skin. Usually the portion of the surface area defined by the hydrated silicate will be in the range of about 0.1 to 20%, more usually 0.5 to 10%.

The drugs that may be used in the matrixes of this invention are hydrophilic and are dissolved in the aqueous component of the hydrated silicate. Correlatively, the drug is substantially insoluble in the hydrophobic polymer component of the matrix and hence no. significant amount of drug is dissolved in that polymer. The amount of drug present in the matrix will depend upon the amount of aqueous component present in the matrix and the solubility of the drug in that component. It will normally constitute 1% to 20% by weight of the matrix. The concentration of drug in the aqueous component of the matrix will be at or below saturation.

Examples of hydrophilic drugs that may be used in the matrixes of the invention are, without limitation, nicardipine hydrochloride, methylsalicylic acid, nitroglycerine, hydrophilic serotonin 5-HT$_3$ receptor antagonists such as ondansetron (sold under the brand name ZOFRAN) and granisetron, aminotetralins such as S(-)-2-(N-propyl-N-2-thienylethylamine)-5-hydroxytetralin, and those drugs disclosed on pages 4–6 of European Patent Application Pub. No. 0452837A2 (Application No. 91105933.5).

The matrix also contains a dispersing agent which aids in maintaining the particulate phase dispersed in the continuous phase. Anionic, cationic, amphoteric or nonionic dispersing agents may be used. Preferably, the dispersing agent is a nonionic surfactant. Examples of such dispersing agents are polyethylenepolyoxypropylene glycol copolymers (sold under the PLURONIC trademark), polyoxyethylene sorbitan esters (sold under the TWEEN trademark) such as polyoxyethylene sorbitan monolaurate, polyoxyethylene sorbitan monopalmitate, polyoxyethylene sorbitan monostearate, and polyoxyethylene sorbitan monooleates, and sorbitan esters (sold under the SPAN trademark) such as sorbitan monolaurate, sorbitan monostearate, and sorbitan monooleate. The dispersing agent will normally constitute 0.5% to 10% by weight of the matrix, more usually 3% to 6% by weight of the matrix.

The matrixes of the invention may be prepared by dissolving the drug in water and optionally other hydrophilic polar solvents and contacting the hydrophilic particulate material with the resulting solution to permit the aqueous solution to be absorbed by the particulate material. This mixture will typically have the texture of a paste. The hydrophobic components of the matrix and the dispersing agent, preferably in admixture, are added to the paste with vigorous mixing to form a viscous dispersion. This dispersion may be formed into appropriate shapes and excess solvent removed therefrom. When the matrix is to be part of a transdermal or transbuccal patch, the hydrophobic domain will normally possess pressure sensitive adhesive properties and the matrix will be cast as a layer or film onto a backing layer. Materials for forming backing layers are well-known in the transdermal patch art and are amply exemplified in the transdermal patch patent literature. Typically, the patch will include a basal release liner layer that is removed prior to use to expose the matrix. A simple and typical transdermal patch structure, generally designated 10, is shown in FIG. 1 wherein 11 designates the backing layer, 12 the matrix layer, and 13 the release liner layer.

In addition to being useful as a component in transdermal or buccal patches, the matrixes of the invention may be formed into tablets for oral administration of the drugs or into inserts or implants for releasing drug into body cavities or within tissues.

The invention is further illustrated by the following examples. These examples are not intended to limit the invention in any manner. Unless indicated otherwise, percentages are by weight.

EXAMPLE 1

Drug Formulation

A matrix composed of 4% of the hydrophilic drug (R)-(-)-N-(1-Methyl-4-(3-methylbenzyl)hexahydro-1H-1,4-diazepin-6-yl)-1H-indazole-3-carboxamide dihydrochloride, 10% propylene glycol monolaurate (PGML), 20% propylene glycol (PG), 20% distilled water, 7% calcium silicate powder (MICRO-CEL E) and 2% nonionic surfactant (PLURONIC L-121) in a polydimethylsiloxane adhesive (Dow Corning Silicone 2920) was prepared by dissolving the drug in the PG and water, mixing the solution with the calcium silicate powder to form a paste, and vigorously mixing the paste with a mixture of the adhesive, PGML and surfactant to form a viscous dispersion.

The dispersion was cast onto a 25 micron thick polyester film (silicone-coated MELINEX 329 from ICI) to a thickness of 250 microns using a Gardener knife and the composite was dried in an oven at 70° C. for 30 min to remove excess solvent. After cooling, the composite was laminated onto a 75 micron thick polyester backing (3M, 1022).

For comparison purposes, the drug was formulated in various single phase matrixes and formed into laminated composites as above.

Skin Flux Testing

Human epidermis was obtained from the full thickness skin which was frozen prior to being separated. Separation of the skin at the dermal/epidermal junction was achieved by immersing the skin in water at 60° C. for two minutes, and then teasing off the dermis. The heat separated epidermis was stored at 20° C. pending use.

Vertically aligned diffusion cells with a diffusional area of 0.71 cm$^2$ and a receiver fluid of 8.0 ml were used. A pH 5.0 phosphate buffer was chosen as a receiver fluid to ensure an infinite sink condition being maintained because this buffer solution exhibited reasonable solubility for the drug. Skin flux studies were conducted for a period of 30 hours.

A 1 ¾ cm diameter section of separated epidermis was punched and mounted in the diffusion cell with the stratum corneum facing the donor compartment. The laminated composites were punched out in 1 ¾ cm diameter circles. After peeling from the releasing side of polyester film, the drug matrix was then mounted between two compartments of the diffusion cell.

After a designated time period has elapsed, a 1 ml sample was taken from the receiver compartment with a micropipette from a given diffusion cell. An equivalent amount of receiver solution was added in the receiver chamber to maintain a constant volume. Dilution of the receiver medium was taken into account when processing the permeation data. Table 1 below reports the results of these skin flux tests. Flux is reported as the average flux over 30 hrs.

TABLE 1

| Formulation | Skin Flux ($\mu$g/cm2/hr) |
|---|---|
| Single Phase Comparisons | |
| 2% drug in Silicone 2920 adhesive | 0 |
| 2% drug in MORSTIK 607[1] adhesive | 0 |
| 2% drug in GELVA 788[2] adhesive | 0 |
| 2% drug, 10% PGML, 10% m-Pyrol in Silicone 2920 adhesive | 0.5 |
| 2% drug, 10% PGML, 10% m-Pyrol in MORSTIK 607 adhesive | 0 |
| 4% drug, 20% PGML, 20% m-Pyrol in KRATON 36-6172[1] adhesive | 0.8 |
| Two-Phase | |
| 4% drug, 10% PGML, 20% PG 20% Dist. water, 7% MICRO-CEL E 2% PLURONIC L-121 in Silicone 2920 adhesive | 17.1 |

1 MORSTIK is an acrylate adhesive.
2 GELVA 788 is an acrylate adhesive.
3 KRATON 36-6172 is a styrene-butadiene copolymer adhesive.

As shown in Table 1, the skin flux of the drug from the two-phase matrix of the invention was vastly greater than the skin flux from any of the comparison single-phase matrixes tested.

EXAMPLES 2–6

These examples illustrate variations of the two-phase matrix formulation of Example 1 in which the proportions of the components differ. These matrixes were prepared and tested as in Example 1. Table 2 below provides details of the compositions of these matrixes and the results of the skin flux tests on them.

TABLE 2

| Example No. | Formulation | Skin Flux ($\mu$g/cm2/hr) |
|---|---|---|
| 2 | 4% drug, 10% PGML, 30% PG 29% Dist. water, 7% MICRO-CEL E, 3% PLURONIC L-121 in Silicone 2920 | 15.7 |
| 3 | 4% drug, 15% PGML, 20% PG, 10% Dist. water, 7% MICRO-CEL E, 3% PLURONIC L-121 in Silicone 2920 | 9.1 |
| 4 | 6% drug, 6% PGML, 30% PG, 20% Dist. water, 7% MICRO-CEL E, 3% PLURONIC L-121 in Silicone 2920 | 20.4 |
| 5 | 6% drug, 6% PGML, 50% PG, 20% Dist. water, 8% MICRO-CEL E, 3% PLURONIC L-121 in Silicone 2920 | 23.9 |
| 6 | 6% drug, 12% PGML, 30% PG, 26% Dist. water, 8% MICRO-CEL E, 3% PLURONIC L-121 in Silicone 2920 | 25.7 |

EXAMPLES 7–8

These examples illustrate two-phase matrix formulations similar to those of Examples of 1–6 but using a different silicone adhesive (Dow Corning 4201). The matrixes were prepared and tested as in Example 1. Table 3 below provides details of the compositions of these matrixes and the results of the skin flux tests on them.

TABLE 3

| Example No. | Formulation | Skin Flux ($\mu$g/cm2/hr) |
|---|---|---|
| 7 | 4% drug, 15% PGML, 20% PG 10% Dist. water, 7% MICRO-CEL E, 3% PLURONIC L-121 in Silicone 4201 | 12.0 |
| 8 | 2% drug, 5% PGML, 20% PG, 15% Dist. water, 2% MICRO-CEL E, 3% TWEEN in Silicone 4201 | 5.4 |

EXAMPLES 9–12

These examples illustrate matrixes similar to that of Example 1 in which the hydrophobic solvent was different than PGML. The matrix formulation consisted of 4% drug, 20% PG, 15% distilled water, 7% calcium silicate, 2% TWEEN 80 surfactant and the indicated % of hydrophobic solvent in polydimethylsiloxane adhesive (Dow Corning 4201). The matrixes were prepared and tested as in Example 1. Table 4 below provides details on the composition and amount of the hydrophobic solvent and the results of the skin flux tests.

TABLE 4

| Example No. | Hydrophobic Solvent | Skin Flux (μg/cm2/hr) |
|---|---|---|
| 9 | 12% PEGML, 3% IPM | 6.4 |
| 10 | 10% Oleyl Oleate | 2.1 |
| 11 | 10% Oleic Acid | 2.0 |
| 12 | 10% Oleyl Alcohol | 9.6 |

EXAMPLES 13–14

These examples illustrate matrixes similar to that of Example 1 in which the silicates other than MICRO-CEL E were used. These matrixes were prepared and tested as in Example 1. Table 5 below provides details of the compositions of these matrixes and the results of the skin flux tests.

TABLE 5

| Example No. | Formulation | Skin Flux (μg/cm2/hr) |
|---|---|---|
| 13 | 2% Drug, 5% Oleyl Alcohol, 20% PG, 15% Dist. water, 1% Talc, 3% TWEEN 80 in Silicone 4201 | 2.1 |
| 14 | 2% Drug, 5% Oleyl Alcohol, 20% PG, 15% Dist. water, 1% Kaolin, 3% TWEEN 80 in Silicone 4201 | 1.2 |

EXAMPLE 15

S(-)-2-(N-propyl-N-2-thienylethylamine)-5-hydroxytetralin is a selective $D_2$ agonist for treating Parkinson's disease. The effective dose for treating Parkinson's disease is estimated to be in the range of about 1 to 3 μg/kg/hr. Accordingly, for transdermal administration, the target flux of this drug (based on a 20 cm$^2$ delivery area) is estimated to be in the range of approximately 3–10 μg/cm$^2$/hr.

Skin flux studies of this drug from various liquid formulations showed that fluxes at or above the effective range could be achieved from saturated solutions of the drug in pH 6.0 buffer or PGML. Similar studies of the flux of this drug from simple matrix systems in which the drug and PGML were formulated in various adhesives (silicone, polyisobutylene, or MORSTIK 607 acrylate) did not provide effective flux levels.

In contrast a series of five two-phase matrix formulations of this drug were prepared in accordance with the present invention. Table 6 below presents the composition of those matrixes and the results of the flux tests thereon.

TABLE 6

| Matrix | 1 | 2 | 3 | 4 | 5 | 6 | 7 | 8 | Skin Flux (μg/cm2/hr) |
|---|---|---|---|---|---|---|---|---|---|
| A | 2 | 10 | 5 | 5 | 10 | 4 | 3 | 61 | 6.41 ± 0.13 |
| B | 4 | 10 | 5 | 5 | 10 | 4 | 3 | 59 | 14.2 ± 0.6 |
| C | 4 | 0 | 5 | 5 | 10 | 4 | 6 | 66 | 8.66 ± 0.19 |
| D | 4 | 5 | 5 | 5 | 10 | 4 | 5 | 62 | 15.5 ± 0.19 |
| E | 4 | 10 | 5 | 5 | 10 | 2 | 3 | 61 | 13.7 ± 1.2 |

1 = Drug (%)
2 = PGML (%)
3 = Benzyl alcohol (%)
4 = PG (%)
5 = pH 6.0 phosphate buffer (%)
6 = MICRO-CELL E (%)
7 = SPAN 60 Emulsifier (%)
8 = Silicone 4201 Adhesive (%)

As indicated, all five of the two-phase matrixes provided fluxes at or above the target level.

EXAMPLE 16

Based on the results of Example 15, two optimized formulations of S(-)-2-(N-propyl-N-2-thienylethylamine)-5-hydroxytetralin. These formulations lacked any PGML, benzyl alcohol or PG. One contained 4% drug, 20% phosphate buffer (pH 6.0), 4% MICRO-CELL E, 4% SPAN 60 emulsifier, and 4% silicone medical fluid 360 (Dow Corning) in silicone 4201 adhesive. The other contained 5% drug, 18% buffer, 5% MICRO-CELL E, 4% SPAN 60 emulsifier, and 4% silicone medical fluid 360 in silicone 4201 adhesive. The flux from these formulations was comparable to those from matrixes B, D, and E of Example 15.

Modifications of the above modes for carrying out the invention that are obvious to those of skill in pharmaceuticals, sustained release formulation, transdermal drug delivery, polymers, pressure sensitive adhesives, and related fields are intended to be within the scope of the following claims.

We claim:

1. A sustained release drug formulation comprising a matrix of:
   (a) a continuous hydrophobic adhesive polymer phase;
   (b) a particulate phase dispersed in the continuous polymer phase comprised of:
      (i) a hydrated calcium silicate comprising calcium silicate and an absorbed aqueous phase;
      (ii) a water-soluble drug at least partly dissolved in the aqueous phase of (i); and
   (c) a dispersing agent for dispersing (b) in (a), wherein the particulate phase defines at least a portion of the surface area of the matrix and provides a diffusion pathway for the drug in the matrix.

2. The sustained release drug formulation of claim 1 wherein the drug constitutes about 1% to 20% by weight of the matrix, the calcium silicate (unhydrated) constitutes about 2% to 20% by weight of the matrix, and the hydrophobic polymer phase constitutes about 30% to about 95% by weight of the matrix.

3. The sustained release drug formulation of claim 1 wherein the hydrated calcium silicate contains 15% to 600% of its own weight in absorbed aqueous phase.

4. The sustained release drug formulation of claim 2 wherein the hydrated calcium silicate contains 100% to 500% of its own weight in absorbed aqueous phase.

5. The sustained release drug formulation of claim 1 wherein said portion constitutes 0.1% to 20% of the surface area of the matrix.

6. The sustained release formulation of claim 1 wherein the hydrophobic polymer phase includes a hydrophobic solvent.

7. The sustained release formulation of claim 6 wherein the hydrophobic solvent is a skin permeation enhancer.

8. The sustained release formulation of claim 7 wherein the hydrophobic solvent is a fatty acid, a fatty acid ester, a fatty alcohol, or a terpenoid.

9. The sustained release formulation of claim 1 wherein the hydrated calcium silicate includes an absorbed polar solvent that increases the solubility of the drug in water.

10. The sustained release drug formulation of claim 9 wherein the polar solvent is ethanol, propylene glycol, low molecular weight polyethylene glycol, isopropyl alcohol, butanediol, m-pyrol, or benzyl alcohol.

11. The sustained release formulation of claim 1 wherein the drug is (R)-(-)-N-(1-Methyl-4-(3-methylbenzyl) hexahydro-1H-1,4-diazepin-6-yl)-1H-indazole-3-carboxamide dihydrochloride, ondansetron, granisetron, or S(-)-2-(N-propyl-N-2-thienylethylamine)-5-hydroxytetralin.

12. The sustained release drug formulation of claim 2 wherein, the hydrophobic polymer is a silicone, the matrix includes propylene glycol and propylene glycol monolaurate, and the water soluble drug is (R)-(-)-N-(1-Methyl-4-(3-methylbenzyl) hexahydro-1H-1,4-diazepin-6-yl)-1H-indazole-3-carboxamide dihydrochloride or S(-)-2-(N-propyl-N-2-thienylethylamine)-5-hydroxytetralin.

* * * * *